United States Patent [19]

Kaminski et al.

[11] Patent Number: 4,975,528

[45] Date of Patent: Dec. 4, 1990

[54] PROCESS FOR SEPARATION AND CONCENTRATION OF APOLIPOPROTEINS USING PERFLUOROCARBON EMULSION

[75] Inventors: Edward A. Kaminski; Albert J. Owen, both of West Chester, Pa.

[73] Assignee: Affinity Biotech, Inc., Malvern, Pa.

[21] Appl. No.: 420,097

[22] Filed: Oct. 16, 1989

Related U.S. Application Data

[63] Continuation-in-part of Ser. No. 334,408, Apr. 7, 1989, abandoned, which is a continuation-in-part of Ser. No. 285,566, Dec. 16, 1988, abandoned.

[51] Int. Cl.$^5$ .............................................. C07K 15/16
[52] U.S. Cl. ..................................... 530/359; 530/375
[58] Field of Search ................ 530/359, 375; 514/746, 514/756

[56] References Cited

U.S. PATENT DOCUMENTS 3,828,017  8/1974  Finley et al. ......................... 530/375
3,911,138  10/1975  Clark, Jr. ............................. 514/746
4,105,798  8/1978  Moore et al. ........................ 514/756

Primary Examiner—Howard E. Schain
Attorney, Agent, or Firm—J. Edward Hess; Donald R. Johnson

[57] ABSTRACT

Lipoproteins are separated from their aqueous solutions, e.g., blood, by treatment with PFC emulsified with phospholipid and then separating the emulsion containing the apolipoproteins. The latter are readily separated from the emulsion.

11 Claims, No Drawings

PROCESS FOR SEPARATION AND CONCENTRATION OF APOLIPOPROTEINS USING PERFLUOROCARBON EMULSION

CROSS REFERENCE TO RELATED CASE

This application is a continuation-in-part of U.S. Ser. No. 334,408, filed Apr. 7, 1989, which is a continuation-in-part of U.S. Ser. No. 285,566, filed Dec. 16, 1988, both of which are in the name of Edward A. Kaminski and Albert J. Owen, and both now abandoned.

BACKGROUND OF THE INVENTION

The effect of lipoproteins in the blood on atherosclerosis is known. When blood cholesterol is high, increasing the risk of atherosclerosis, there is usually an increase in the low-density lipoprotein, LDL, the so-called "bad" cholesterol. High-density lipoproteins (HDL) appear to remove excess cholesterol from the bloodstream and are thus referred to as the "good" cholesterol. Recent work suggests that the HDL-LDL differentiation is not sufficiently precise and some workers are now using other categories; very low density lipoproteins (9VLDL), intermediate density lipoprotein (IDL), etc. The point is that different lipoproteins contribute differently, even within the above gross subdivisions, to the onset and progression of atherosclerosis. Accordingly, a method of quickly identifying the proteins in the bloodstream is advantageous.

Currently, the apolipoproteins are isolated from blood or plasma by density gradient ultracentrifugation followed by organic solvent extraction of the lipid portion of the lipoprotein. The procedure is usually limited by the lengthy period required for the ultracentrifugation step (12-24 hours), as well as by the number of samples that can be processed at any one time. Because of these constraints, only problem patients receive this type of blood analysis.

There are other instances, as well, where it is desired to separate proteins from aqueous solutions thereof. For example, the manufacture of apolipoproteins or other lipid binding proteins by microbiological processes, or their isolation from other biological sources, usually involves an aqueous fermentation or extraction media from which the produced proteins must be recovered. Our invention is nicely applicable to this situation as well.

SUMMARY OF THE INVENTION

Our invention provides a rapid and efficient method of separating lipoproteins from their aqueous solutions such as blood. Blood is first mixed with an aqueous perfluorocarbon (PFC) emulsion, i.e. a PFC dispersion, containing a phospholipid emulsifier. The lipoproteins attach to the phospholipid coating on the surface of the PFC particles. The emulsion is then separated from the blood and the apolipoproteins in the emulsion are identified by known analytical procedures, either with or without prior separation of the proteins from the PFC emulsion. This PFC-emulsion separation technique allows the whole separation to be done in less than an hour.

DETAILED DESCRIPTION OF THE INVENTION

Although, as noted above, the invention is applicable to aqueous solutions generally, it will be described in reference to blood or plasma because that is one of its principal applications. The term plasma will be used herein as encompassing both terms except where they are not equivalent, in which case the difference will be pointed out.

The perfluorocarbon emulsion used in the invention is any of those well known in the art. See, e.g., U.S. Pat. No. 4,105,798 and 3,911,138, which are hereby incorporated by reference. The emulsions are described in more detail as follows.

The perfluorocarbon in the emulsion is generally a perfluorocyclocarbon, i.e., a cyclic compound of carbon which may or may not contain acyclic or alkyl side chains. The compound may be mono, di or polycyclic, as with cyclohexane or the perhydro derivatives of naphthalene and phenanthrene, but usually has no more than 4 rings, preferably 2-3. For effective use as a blood substitute the cyclocarbon usually has 9-12 carbon atoms, but since we are not using the emulsion for such purpose, this limitation is not as critical. Perfluorocarbon means that at least 50%, preferably at least 80%, more preferably at least 99% of the hydrogen atoms have been replaced with fluorine.

Typical compounds of the type described above are the perfluoro derivatives of trimethylcyclohexane, isopropylcyclohexane, tetramethylcyclohexane, 1-methyl-4-isopropylcyclohexane, n-butylcyclohexane, decahydroacenaphthene, decalin, methyl and dimethyldecalins, tetradecahydrophenanthrene, dodecahydrofluorene, and diisopropylcyclohexane.

Preferred cyclocarbons are non-aromatizable polycyclic perfluoro compounds having two bridgehead carbon atoms linked through a bridge containing at least one carbon atom. By the term "bridgehead carbon atom" is meant a carbon atom bonded to three other carbons in a cyclic compound having 2 or more rings. By the term "non-aromatizable" is meant a polycyclic perfluoro compound whose ring structure cannot be aromatized without destruction of its original carbon-to-carbon cyclic bonds. These preferred compounds are distinguished from perfluorodecalin and others mentioned above which can be aromatized. Examples of these preferred compounds are the perfluoro derivatives of such $C_9$–$C_{12}$ polycyclic compounds as bicyclononanes (e.g., bicyclo[3.3.3]nonane, 2,6-dimethylbicyclo[3.3.1]nonane or 3-methylbicyclo[3.3.1]nonane), adamantane, methyl and dimethyladamantane, ethyladamantane, tetrahydrodicyclopentadiene, methyl and dimethylbicyclooctanes, pinane, camphane, 1,4,6,9-dimethanodecalin, bicyclo[4.3.2]undecane, bicyclo[5.3.0]decane and the like, or mixtures thereof. They can be made by known means. Compounds of this preferred type are described in U.S. Pat. No. 4,105,798.

Certain, acyclic perfluorocarbons have also been used, or evaluated for use, in medical applications, most notably perfluorotributylamine, perfluorooctane, 1,1,2-trihydroperfluoro-1-decene, 1,1,1,2,2-pentahydroperfluorodecane and the like.

The emulsifier we use is phospholipid, preferably a lecithin, which is a pharmaceutically acceptable article of commerce. It has been approved by the FDA for use as an emulsifier in various medical products. Preferably the phospholipid is egg yolk phospholipid (EYP), and, for convenience, the invention will be described with this material.

The PFC emulsion generally contains 5–50 v % PFC, preferably 10–40 v %. The particle size of the PFC is generally less than 0.2 micron, preferably 0.1, but this is for in vivo uses of the emulsion and is not as critical in our process as long as the emulsion is stable for the duration of its use.

The amount of phospholipid is generally 1-10 w/v %, preferably 2-5 w/v %. As is well known, the amount depends somewhat on the amount of PFC and the size of the PFC particles.

It is known that in a PFC emulsion the surfactant distributes itself with a portion being on the surface of the PFC particles and the remainder, the "excess", being in the aqueous phase. It is desirable to remove this "excess" because it competes with that on the PFC particle for the apolipoproteins. Any apolipoprotein which is combined or attracted to the "excess" may not be captured in the subsequent processing involved in our invention. Any such "lost" apolipoprotein does not preclude a satisfactory qualitative analysis using our invention, but it would disadvantage a quantitative analysis.

The excess surfactant can be removed by centrifuging to spin off the aqueous phase of the emulsion, reconstituting, with fresh aqueous phase, the remaining emulsion gel which contains the portion of surfactant on the PFC particles, and then repeating this centrifuging-reconstituting procedure until the "excess" surfactant is adequately removed. This procedure is described in more detail in South Africa Patent No. 2544/85, Dec. 24, 1985. Preferably the amount of surfactant in the aqueous phase in the emulsion, i.e., the amount which can be removed by centrifuging, is less than 35% of the total surfactant in the emulsion, preferably less than 15%, more preferably less than 10% by weight.

The emulsion is first mixed with the animal blood to be tested, either externally with a withdrawn blood sample, or by infusion and subsequent withdrawal from the animal of a blood/emulsion mixture.

Generally the amount of emulsion should be about 25 v % of the amount of blood being treated, when an emulsion containing 25 v % PFC and 2.5 w/v % EYP is used and the emulsion particles are 0.2-0.3 micron. Since the lipoprotein attaches to the EYP which coats the PFC particles in the emulsion, the emulsion:blood ratio will vary depending on these variables as well as the PFC employed, etc. It is generally desired to remove all the blood lipoprotein and whether this has been done is readily determined by analyzing the blood remaining.

The blood/emulsion mixture is then treated to separate the PFC particles which now contains the lipoproteins. This is most readily done by centrifuging at 5,000-20,000 Gs for 5-10 minutes. At the end, an emulsion gel is at the bottom of the centrifuge tube with the blood above. The emulsion is a gel because some of the original water is now in the blood phase, the remainder being part of the tightly bound water-EYP-PFC phase.

If blood rather than plasma is used, it will be found after this centrifuging that the emulsion gel is red because the hemoglobin spins into the gel. This can be prevented by initially layering the blood/emulsion mixture onto a dense (e.g., 2-3M) sucrose solution. This sucrose solution will restrain the hemoglobin to the blood layer in the centrifuge tube, and at the end of the centrifugation the tube will contain the blood layer above the sucrose layer which is above the emulsion gel.

During this initial separation described above, the lipid portion of the lipoproteins surfaces to the top of the plasma layer. Consequently, it is the apolipoproteins which are attached to the EYP coating on the PFC particles.

The emulsion gel is separated and is preferably washed with 2-3 times its volume of physiological saline. This effects the removal of protein and the other matter trapped within the interstices of the gel. The gel-NaCl solution mixture is shaken and then centrifuged as before, after which the washed gel is separated. It is worthy of note that the proteins removed in this washing step are not lipoproteins for which the separation is being made.

The next step is to separate the apolipoproteins from the emulsion gel, i.e., from the fluorocarbon. This is easily done by washing or mixing the gel with a commercially available detergent such as a $C_{5-20}$ alkyl sulfonate, e.g., sodium dodecylsulfonate (SDS Reducing Buffer). The detergent solution should be 0.5-10 w/v % preferably 1-5 w/v %. Preferably this is done at an elevated temperature of 50°-95° C. to speed the dissolution of the protein in the detergent. Another suitable detergent for this purpose is NP-40, a commercially available octylphenol-ethylene oxide condensate, in which case a lower temperature, e.g., 20° C., can be used and a lower concentration of detergent, e.g., 0.05 w/v %, is suitable. For either detergent, a volume ratio of 0.0001-1.0 preferably 0.001-1.0 more preferably 0.001-0.01 liter of detergent solution per gram of gel is usually adequate. The protein is on the surface of the PFC particle so that relatively little detergent liquid is required.

The SDS solution of the apolipoproteins is then analyzed by polyacrylamide gel electrophoresis (generally known as SDS-PAGE) or by antibody techniques. Both of these procedures are known for this purpose.

EXAMPLE 1

A 250 g. male, Sprague-Dawley rat was infused with 20 ml./kg of a PFC emulsion. Such rats contain about 20 ml. blood. The emulsion contained 25 w/v % perfluoromethyladamantane, 2.4 w/v % EYP, balance water and had an average particle size of 0.25±0.03 microns. The emulsion was adjusted with NaCl to an osmotic pressure of 300 milliosmoles.

After 3 hours, 0.5 ml. blood was removed from the rat and layered over 1 ml. of 2M sucrose solution in a centrifuge tube. Then followed centrifuging at 12,000 Gs for 10 min. at 5° C. The gel at the bottom of the tube was separated with pinch clips. It weighed 15 mg. It was resuspended in 1 ml. of 0.9 w % clinical NaCl solution, shaken and recentrifuged at 12,000 Gs for 10 min. at 5° C., after which 15 mg. of gel were separated from the aqueous phase.

The separated gel was mixed with 2% SDS Reducing Buffer at 90° C. for 5-10 minutes. The buffer was made by combining the following ingredients in the amounts indicated and then adding 7.75 mg. per ml. of DTT (dithiothreitol)

| Distilled water | 5.2 vol. |
|---|---|
| 0.5 Tris-HCL, pH 6.8 | 1.0 vol. |
| 10% (w/v) SDS | 1.6 vol. |
| 0.05% (w/v) bromohenol blue | 0.2 vol. |

The detergent layer was centrifuged in the same manner as before, yielding an aqueous supernate containing the SDS and the apolipoprotein and a lower gel layer devoid of protein. The separation took 45 minutes.

SDS-PAGE and antibody methods identified the following proteins. The amounts of the proteins can be quantified by scanning the SDS-PAGE gel with a commercially available densitometer.

| Apolipoprotein | Mol. Wt. (1000) |
|---|---|
| SDS-PAGE | |
| A-I | 28.0 |
| A-II | 17.4 |
| C-I | 6.6 |
| C-II | 8.8 |
| C-III | 8.8 |
| E | 34.0 |
| Antibody | |
| Proteins Found: | A-I, A-II, B-100, B-48, C-III and E. the two B proteins have molecular weights above the maximum allowable (about 200,000) for SDS-PAGE. No antibodies were available for proteins C-I and C-II |

The above apolipoproteins found are the ones known to be in the rats tested, which demonstrates the accuracy of the test.

EXAMPLE 2

10 mls of an emulsion of the same composition and particle size as in EXAMPLE 1 was centrifuged at 12,000 gs for 15 minutes at 10° C. The supernatant was discarded and the emulsion gel (3 ml.) was resuspended in phosphate buffered saline solution (pH 7.4). This procedure was repeated twice more to provide a final emulsion generally free of aqueous phase surfactant.

Next, Spraque-Dawley rat plasma was centrifuged at 1500 gs for 15 minutes at 5° C. to remove any precipitate that might be present. Then, 0.5 ml. portions of the above emulsion were combined with the plasma to yield emulsion:plasma ratios of 1, 2, 4 and 8:1. Then followed the centrifuging, gel separation, resuspension, shaking, recentrifuging, and final gel separation as described above in EXAMPLE 1. The sucrose layering step of EXAMPLE 1 was not employed because plasma is used in this EXAMPLE 2 rather than whole blood.

The separated gel was processed in the same manner as in EXAMPLE 1 and the same proteins identified.

EXAMPLES 3-5

The procedure described above in EXAMPLE 1 was repeated in essentially the same manner with New Zealand white rabbits, C3J mice and a generic bovine plasma. The results were essentially the same. Since the cross-reactivity of these blood proteins, and the blood in EXAMPLE 1, is very close to human blood, the applicability of the procedure to human blood is very likely ensured.

We have also found several means of improving the extraction efficiency above that which is obtained following the procedures described above. Indeed, we can often utilize one or more of these techniques to achieve quantitative extraction levels of certain apolipoproteins.

The first is to add a small quantity of surfactant to the blood, which seems to "loosen up" the proteins from other blood components and make them more susceptible to extraction. Both ionic and nonionic surfactants may be employed such as NP-40 (a polyoxyethylene alkyl phenol) or sodium deoxycholate. Only small amounts are usually necessary, 0.05-1% (w/v), but up to 5% can be used if desired.

The second technique is to add either phosphatidic acid (I) or lysophospholipid (II) to the emulsion. Either the alpha or beta isomers of each are suitable. Adding I improves the extraction principally of apolipoprotein A-I, whereas the principal effect of adding II is to improve the extraction of apolipoprotein B-100.

When used, these materials are preferably incorporated into the emulsion by addition to the aqueous phase when the phospholipid is added. Thus, when the finished emulsion is spun down and reconstituted, to remove excess lipid from the aqueous phase, these materials, which themselves are lipids, are also removed from the aqueous phase.

Table I shows the advantages of these techniques in experiments with control sera (Sigma Corp.) containing known amounts of apolipoproteins, as well as with pure apolipoprotein. In Runs 1-6, the purchased sera was diluted with water to 25 micrograms of sera per ml of water. In Runs 7-11, the pure B-100 was diluted to 1.25 micrograms per ml of water and in Run 12 to 1.33 micrograms per ml of water. The PFC emulsion is the same as used in Example 2. The amount of I, II, and cholesterol added to the emulsion is in w/v % and is as indicated in the Table. The cholesterol is added merely to determine its effectiveness but the results show it provides no benefit. The buffers used are as indicated, the phosphate buffer being at a level of 25 mmoles/l and the MOPS (morpholinopropanesulfonic acid) being at a level 10.0 mmoles/l.

Run 1 shows that the basic phospholipid extraction described earlier herein allows the detection of A-I and B-100 but does not provide a quantitative extraction. Runs 2 and 3 show the lack of effect of cholesterol.

Runs 4, 5, and 6 show the improved extraction of A-I and B-100 from sera due to the addition of I. The plus sign (+) in the last column indicates a significant increase in A-1 extraction over the Run 1 result, but with less than 50% being bound. Run 5 had the additional benefit of 0.025 w/v % NP-40 added to the sera before the extraction.

Runs 7-11 show that the addition of II improves the extraction of B-100 from aqueous solutions of pure B-100. Run 12 shows the same benefit when sera is employed. It should also be noted that the emulsions in Runs 10-12 were not heat sterilized.

TABLE 1
(EXAMPLE 6)

| | | | | | | % BOUND | |
| RUN | EMULSION | I | II | CHOLESTEROL | BUFFER | A-I | B-100 |
|---|---|---|---|---|---|---|---|
| 1 | 1433 | — | — | | Phosphate | Less Than 1% Each | |
| 2 | 1151 | — | — | 0.2 | Phosphate | Less Than 1% Each | |
| 3 | 1152 | — | — | 0.4 | Phosphate | Less Than 1% Each | |
| 4 | 1155 | 0.1 | — | — | None | + | <1 |
| 5 | 1157 | 0.3 | — | — | None | >70 | 11 |
| 6 | 1159 | 0.1 | — | — | Phosphate | + | <1 |
| 7 | 1194 | - | .05 | 0.4 | MOPS | | 50 |
| 8 | 1195 | .05 | .05 | 0.4 | MOPS | | 60 |

TABLE 1-continued (EXAMPLE 6)

| RUN | EMULSION | I | II | CHOLESTEROL | BUFFER | % BOUND A-I | B-100 |
|---|---|---|---|---|---|---|---|
| 9 | 1196 | — | .05 | — | MOPS | | 40 |
| 10 | 1194 | — | .05 | 0.4 | MOPS | | 100 |
| 11 | 1195 | .05 | .05 | 0.4 | MOPS | | 100 |
| 12 | 1196 | — | .05 | — | MOPS | | 100 |

The invention claimed is:

1. Method of separating lipoprotein present in an aqueous solution thereof which comprises mixing the solution with an emulsion of perfluorocarbon particles in water containing phospholipid, whereby the protein portion of said lipoprotein binds to phospholipid on the surface of the perfluorocarbon particles, and separating phospholipid-protein-containing perfluorocarbon from said aqueous solution.

2. Method according to claim 1 wherein said separated perfluorocarbon is further treated with aqueous ionic or nonionic surfactant to separate protein therefrom.

3. Method according to claim 1 wherein said aqueous solution is blood or plasma.

4. Method according to claim 1 wherein the separated fluorocarbon is further treated to identify the proteins therein.

5. Method according to claim 1 wherein the emulsion additionally contains lysophospholipid or phosphatidic acid.

6. Method according to claim 5 wherein the emulsion additionally contains lysophospholipid.

7. Method according to claim 5 wherein the emulsion additionally contains phosphatidic acid.

8. Method according to claim 1, 2, 3, 4 and 5 wherein the aqueous phase of said emulsion contains less than 35% of the amount of phospholipid in said emulsion.

9. Method according to claim 3 wherein ionic or nonionic surfactant is added to the blood to improve said binding of protein to phospholipid.

10. Method according to claims 1, 3 or 4 wherein the perfluorocarbon is a fluorohydrocarbon and at least 80% of the hydrogen atoms in the hydrocarbon have been replaced with fluorine.

11. Method according to claims 1, 3 or 4 wherein the perfluorocarbon is a fluorohydrocarbon and at least 99% of the hydrogen atoms in the hydrocarbon have been replaced with fluorine.

* * * * *